United States Patent [19]

Sudmann et al.

[11] Patent Number: 4,913,903

[45] Date of Patent: Apr. 3, 1990

[54] POST-SURGICAL APPLICATIONS FOR BIOERODIBLE POLYMERS

[75] Inventors: Einar Sudmann, Os, Norway; Pieter Bonsen, Los Altos; Eun S. Lee, Redwood City, both of Calif.

[73] Assignee: ALZA Corporation, Palo Alto, Calif.

[21] Appl. No.: 336,555

[22] Filed: Apr. 10, 1989

Related U.S. Application Data

[63] Continuation of Ser. No. 10,881, Feb. 4, 1987, abandoned.

[51] Int. Cl.$^4$ .............................................. A61M 7/00
[52] U.S. Cl. .................................... 424/426; 424/484; 424/423; 424/422
[58] Field of Search ............... 424/426, 427, 428, 433, 424/436, 484, 486, 489, 423, 422; 128/92 R, 924 J

[56] References Cited

U.S. PATENT DOCUMENTS

| | | | |
|---|---|---|---|
| 3,620,218 | 11/1971 | Schmitt et al. | 128/334 R |
| 3,867,190 | 2/1975 | Schmitt et al. | 117/138.8 A |
| 3,875,937 | 4/1975 | Schmitt et al. | 128/156 |
| 3,937,223 | 2/1976 | Roth | 128/325 |
| 3,978,203 | 8/1976 | Wise | 424/22 |
| 3,991,766 | 11/1976 | Schmitt et al. | 128/335.5 |
| 4,070,347 | 1/1978 | Schmitt et al. | 260/77.5 D |
| 4,093,709 | 6/1978 | Choi et al. | 424/19 |
| 4,115,544 | 9/1978 | Shell | 424/428 |
| 4,122,158 | 10/1978 | Schmitt | 424/27 |
| 4,131,648 | 12/1978 | Choi et al. | 424/22 |
| 4,138,344 | 2/1979 | Choi et al. | 252/1 |
| 4,155,992 | 5/1979 | Schmitt | 424/19 |
| 4,180,646 | 12/1979 | Choi et al. | 528/153 |
| 4,300,565 | 11/1981 | Rosensaft et al. | 128/335.5 |
| 4,304,767 | 12/1981 | Heller et al. | 424/426 |
| 4,322,323 | 3/1982 | Capozza | 424/426 |
| 4,346,709 | 8/1982 | Schmitt | 424/426 |
| 4,349,530 | 9/1982 | Royer | 424/19 |
| 4,409,974 | 10/1983 | Freedland | 128/92 B |
| 4,439,420 | 3/1984 | Mattei et al. | 424/78 |
| 4,440,789 | 4/1984 | Mattei et al. | 424/78 |
| 4,506,681 | 3/1985 | Mundell | 128/92 D |
| 4,549,010 | 10/1985 | Sparer et al. | 528/361 |

OTHER PUBLICATIONS

Sudmann et al., "Inhibition of Partial Closure of Epiphyseal Plate in Rabbits by Indomethacin", Acta Orthop. Scand., vol. 53, (1982), pp. 507–511.

Sudmann et al., "The Charnley Versus the Christiansen Total Hip Arthroplasty", Acta Orthop. Scand., vol. 54, (1983), pp. 545–555.

Merck Pamplet on Septopal ® Chain and Septopal ® Beads, "Polymethylmethacrylate Containing the Broad—Spectrum Antibiotic Gentamicin and a Contrast Medium", Received by ALZA Corporation, Aug., 1986, Darmstadt, F. R. Germany.

Primary Examiner—Nancy A. B. Swisher
Attorney, Agent, or Firm—D. Byron Miller; Edward Mandell; Steven F. Stone

[57] ABSTRACT

Applications of bioerodible polymers as surgical "leave behind" products in the areas of orthopedic, thoracic, abdominal, ocular and liver/spleen surgery.

9 Claims, No Drawings

POST-SURGICAL APPLICATIONS FOR BIOERODIBLE POLYMERS

This application is a continuation of application Ser. No. 07/010,881, filed Feb. 4, 1987 now abandoned.

BACKGROUND OF THE INVENTION

1. Field of the Invention

This invention relates to bioerodible polymers. More particularly, this invention relates to bioerodible polymers useful as post-surgical "leave behind" products. Still more particularly, but without limitation thereto, this invention relates to improvements in orthopedic, thoracic, abdominal, ocular and parenchymatous organ surgery.

2. Description of the Prior Art

Bioerodible polymers are well known in the art and have served such purposes as the treatment of burn surfaces Schmitt, U.S. Pat. No. 4,122,158 and for the delivery of numerous beneficial agents Shell, U.S. Pat. No. 4,115,544, both of which are incorporated herein by reference.

The present invention applies the use of bioerodible polymers to the field of post-surgical "leave behind" products where the advantages gained are either from the physical presence of the polymer itself and/or from any beneficial agent which the polymer delivers.

SUMMARY OF THE INVENTION

An object of the present invention is to develop post-surgical uses for bioerodible polymers, in the form of "leave behind" products.

A further object is to improve surgical techniques in the orthopedic, thoracic, abdominal, ocular and parenchymatous organ areas.

A still further object of the present invention is to develop uses for "leave behind" products whose physical presence is beneficial.

An even further object of the present invention is to develop uses for "leave behind" products which are capable of delivering beneficial agents.

These and other objects of the present invention will become more readily apparent from the ensuing specification.

DESCRIPTION OF THE PREFERRED EMBODIMENT

Bioerodible polymers and their method of synthesis are well known in the art. Of particular value to the present invention is a family of polyorthoesters available from the Alza Corporation (Palo Alto, CA) under the trademark "Alzamer®". These polymers are disclosed in U.S. Pat. Nos. 4,070,347, 4,093,709, 4,122,158, 4,131,648, 4,138,344, and 4,155,992, for example, all of which are incorporated herein by reference.

The polyorthoesters are biodegradable vehicles whose properties range from hard solid (glassy) polymers to viscous liquids and they may be fabricated into a variety of physical shapes. They can be used alone with or without an erosion rate modifier, or in conjunction with a drug which is physically dispersed in the matrix and released by diffusion as the polymer erodes.

The polymer itself is eroded by hydrolysis and the breakdown products, which are non-toxic, are either excreted in the urine or incorporated into the Krebs cycle and used for energy. As the polymer is eroded by hydrolysis at a practically zero order rate of decay, the release rate of any drug which has been added to the system, is near constant (zero order kinetics) as it depends upon the vehicle's erosion rate.

The polymers as used in this invention are based upon two polyorthoesters: poly(2,2-dioxy-cis,trans-1,4-cyclohexane dimethylene tetrahydrofuran), which is a hard solid (glassy) polymer having the following structure:

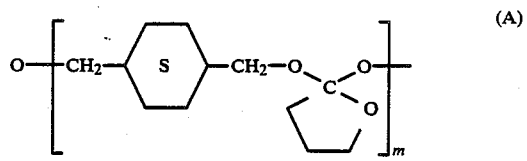

where m equals a number such that the molecular weight of the polymer is within the range of 10,000 to 60,000; and poly(2,2-dioxy-1,6-hexamethylene tetrahydrofuran), which is a viscous polymeric liquid having the following structure:

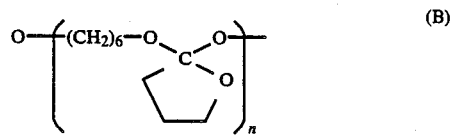

where n equals a number such that the molecular weight of the polymer is within the range of 10,000 to 60,000. Other orthoester polymers with similar physical properties can be substituted for the polymers noted above, and are disclosed in U.S. Pat. No. 4,180,646, which is incorporated herein by reference.

The materials used in the applications of this invention are selected from the group consisting of polymer (A), polymer (B), physical mixtures of polymer (A) and polymer (B), block copolymers of (A) and (B), and random copolymers of (A) and (B). When a hard polymeric substance is desired, a cis-trans mixture of (A) is used. Alternately, when a pliable polymeric substance is used, the viscous (B) is added to the cis-trans mixture of (A). Lastly, when a suspension is desired, polymer (A) or polymer (B) is used.

There are several methods of developing pliable copolymers. The different polymers (A) and (B) can be physically mixed together after polymerization (physical mixture). Alternately, (A) and (B) can be physically mixed together as low molecular weight block polymers and then polymerized further (block copolymers). Lastly, segments of (A) and (B), i.e. the diol fractions, can be mixed in the desired ratio and be reacted together with diethoxytetrahydrofuran and polymerized (random copolymers). These methods are explained in detail in the above referenced patents.

For the purposes of this invention, the terms "polymer foils", "polymer beads" and "hard polymer" as used herein, relate to different physical shapes fabricated from (A) alone. As used herein the term "polymer foil" refers to thin sheets, the term "polymer beads" or "polymer particles" refers to a plurality of spherical shapes and "hard polymer" refers to a solid material which is formed into a desired shape. As used herein, the term "bioerodible bone wax" relates to a pliable material consisting of physical mixtures of polymer (A) and polymer (B), block copolymers of (A) and (B) or random copolymers of (A) and (B). It is similar in consistency to commercially available bonewax. As used herein, the term "leave behind" product relates to biodegradable products to be placed at the site of a surgical procedure just after completion of the surgery for the prevention of infection, the reduction of inflammation and the stopping of bleeding, for example.

As used herein, the term "drug" relates to a chemotherapeutic agent, compound or composition of matter which is administered for the purpose of providing some beneficial or therapeutic effect.

We have found that bioerodible polymers, in particular those with a well-defined erosion rate, are especially suited for use as leave behind products in orthopedic, specifically bone and joint, surgery.

A first application of this invention is in hemostasis. Bone is normally profusely permeated with blood vessels. Therefore, when bone is operatively cut or removed, e.g. for bone grafting, removal of bony excrescences or bony tumors, for gaining access to the spinal cord or brain, in chest surgery when the sternum is split longitudinally or in dental surgery, the bleeding from the cut bone surface has usually been stopped by applying a beeswax/isopropyl palmitate blend onto the bleeding bone. The hemostatic action of this blend is by physical tamponade only, and has no inherent hemostatic quality. This blend is insoluble in the body fluids and acts as a permanent foreign body after implantation, thereby increasing the likelihood of infection or low grade inflammatory reaction at the site of implantation and inhibiting bone formation.

Bioerodible bone wax as disclosed herein, can be formulated to have the same physical properties of the beeswax/isopropyl palmitate blend and so can give hemostasis by physical tamponade. Additionally, bioerodible bone wax is in vivo rapidly permeated by the blood and so has hemostatic properties in itself. Tests in rats have revealed that bioerodible bone wax does not inhibit the healing of fractures nor the filling of bone defects with new tissue.

A second application in the area of orthopedics is in the prevention of osteomyelitis. Application of modern aseptical surgical techniques to the removal of diseased soft and hard bone tissue in conjunction with the systemic use of antibiotics normally will allow for proper healing of the bone. A critical step of this procedure is the filling of the void which has been created. The best filler is autologous bone tissue. However because such bone grafts may become infected, it is advisable to administer antibiotics over a period of several months after the surgical procedure. Polymethylmethacrylate (PMMA) bone cement in the form of beads impregnated with gentamicin has been used. However, PMMA is an acrylic polymer which does not degrade chemically. Therefore, when the drug supply is depleted the PMMA remains in the body as a foreign substance or has to be removed sometime after the surgical procedure.

Polymer beads or particles, as disclosed herein, when impregnated with a chemotherapeutic agent such as an antibiotic, e.g. gentamicin or one of the cephalosporins, can be used to fill the osteomyelitic defect in the bone. These polymer beads provide a constant drug concentration locally over a prolonged period of time until the polymer is resorbed. Thus there is no need for the surgical reintervention for their removal nor should the polymer beads in themselves induce infection. Additionally, the size of the polymer beads can vary for the specific application, using smaller diameter beads when working with small bones such as are present in the hands.

A third application of this invention in the field of orthopedic surgery is in the area of artificial joints. Total hip arthroplasty has become routine for arthrosis of the hip joint. Most joints now can be replaced by artificial ones. However, there is the constant concern over postoperative infection of the artificial joint. To avoid this complication, patients are treated prophylactically with antibiotics systemically and/or locally. In total hip replacement, bone cement is commonly used to fasten the prosthetic devices to the bone. To restrict bone cement to the places where it is needed, a cement restrictor is inserted in the femoral canal and sometimes in the acetabular fossa. Typically, the femoral cement restrictor is made of plastic and the acetabular one is made of stainless steel. Both act as permanent foreign bodies after implantation, which is undesirable. Using a bioresorbable restrictor containing a sustained drug release system, ie. hard polymer impregnated with a chemotherapeutic agent, for example an antibiotic, would serve the same purpose without remaining as a foreign implant. Also, it will provide additional prophylaxis against sepsis in the artificial joint.

As for the bone cement itself, PMMA bone cement impregnated with gentamicin provides adequate drug delivery but is mechanically weakened by the intrusion of blood from the bone surfaces. To avoid this shortcoming, many surgeons dispense with it all together and use expensive, special prosthetic devices which do not require any bone cement. However that still leaves the problems of: providing an effective way of hemostasis in bone, providing for local antibiotic prophylaxis at the implant/bone interface, in the artificial joint proper and in the operative wound in the soft tissue.

Bioerodible polymers can be used in total joint arthroplasties both for purposes of hemostasis and as a means for prophylaxis against infection. Bioerodible bone wax, as disclosed herein, can be used for hemostasis both in cemented and uncemented total joint arthroplasties. Impregnated with a chemotherapeutic agent such as an antibiotic, gentamicin for example, bioerodible bone wax provides the necessary prophylaxis against sepsis at the critical implant/bone interface. Additionally, polymer foils impregnated with an antibiotic or other chemotherapeutic agent will provide the necessary prophylaxis against sepsis in the artificial joint proper and in the wound in the soft tissues. Depending upon the particular location, the hard polymer could be shaped in any desired configuration: a hard collar for use around the neck of the stem in a hip joint, or foils for soft tissue applications, for example. Further use for the hard polymer is in artificial joints inserted without the use of bone cement, where the joint can be pretreated by the bioerodible hard polymer impregnated with an antibiotic/antiseptic drug. This use would be especially suited for application of the hard polymer to prosthetic devices covered with pores on the surface intended for the ingrowth of tissue.

A further application of the bioerodible polymers of this invention is for prolonged drug delivery after arthroscopic surgery. Such prolonged delivery over a 2-5 day period (postoperative convalescence period) decreases pain and complications. The material can be formulated into a suspendable particulate dosage form comprised of particles of the bioerodible polymer (A) and the chemotherapeutic agent to be delivered and injected into the joint. This drug could be for example, an anti-inflammatory agent, an anti-infective agent, a locally acting analgesic, an antispasmodic agent, or any combination of these. The polymer (A)/agent suspension is injected into the surgical site after arthroscopic or other joint surgery. Alternately, a suspension of the chemotherapeutic agent and polymer (B) can be injected into the joint.

Another application of the hard polymer disclosed herein is in the area of leg length discrepancies. Lengthening of the shorter leg is usually done by mechanical distraction. The bone is cut off transversely and the two bone fragments gradually distracted from each other by means of an external fixation device which is anchored to the bone fragments by pins. The likelihood of infection is great because the pins must traverse all soft tissue, including the skin. Shortening of the longer leg is achieved by destroying the growth plate(s) of the limb (epiphysiodesis) or by removing a segment of the bone.

In the area of leg lengthening, the hard polymer of this invention finds particular usefulness when formed in the shape of a sleeve for the percutaneous pins. This sleeve is impregnated with an antibiotic such as gentamicin, which would reduce the need for systemic antibiotics and reduce the risk of local infection. Alternately, the sleeves could be made porous so that in permitting the ingrowth of fibrous tissue, the liklelihood of pin tract infection would be greatly reduced. As for leg shortening, application of the hard polymer impregnated by a vasodilating drug near the growth plate of the shorter leg would stimulate growth by hyperemia, thereby eliminating the necessity of cutting the longer leg.

A fifth application of this invention in the field of bone and joint surgery is in the prevention of unwanted ossification. After injuries or after surgery, unwanted bone can form erratically in the soft tissue surrounding (artificial) joints and in muscle (heterotopic bone formation) or on the bone proper (orthotopic bone formation). Inhibition of bone formation has been obtained by using x-ray irradiation to kill the osteoblasts which form the bone, by systemic use of anti-inflammatory drugs, by fat grafts or by application of a beeswax/isopropyl palmitate blend.

Hard polymer impregnated with a bone formation inhibiting agent such as indomethacin, can be applied locally to effectively inhibit bone formation. This finds particular use in cases of partial closure of the epiphyseal plate, where the bone bridge has been surgically removed and new bone tissue formation in the remaining bone defect is undesirable. This impregnated polymer can also be used in cases of craniosynostosis where the cranium has been separated to allow for normal growth and new bone formation must be inhibited. Additionally, this impregnated polymer is useful in preventing heterotopic bone formation in muscle tissue, which often occurs after spinal injuries and after direct injury of the muscle itself.

A sixth application of the presently disclosed bioerodible polymers is in the area of stimulation of bone formation. By using the hard polymer of this invention impregnated with a bone morphogenetic protein, bone growth can be encouraged. This is useful in fracture treatment where the hard polymer and bone formation stimulating agent can be injected into and/or applied to the bone. Also, this can be used as an artificial bone tissue formulation which can be used to replace missing bone until the bioerodible polymer is replaced by living bone by creeping substitution.

We have also found that bioerodible polymers are especially suited for use as leave behind products in the area of thoracic and open heart surgery.

As noted above, bioerodible bone wax as disclosed herein, is especially suited for use in stopping bleeding. This finds particular application in thoracic and open heart surgery where the sternum is usually split longitudinally to gain access to the interior of the chest and heart.

A second use for the bioerodible polymers in this area is in the treatment of bacterial endocarditis, which if left untreated, is usually fatal. Surgical replacement of the diseased cusps of the heart with artificial ones is followed by close monitoring so as to note and remedy any reinfection which may occur during the critical first postoperative weeks. This has been done by systemic antibiotic therapy. A sustained drug release system capable of providing high concentrations of an anti-infective agent inside the heart itself is an exceptional alternative to systemic antibiotic delivery. Bioerodible bone wax impregnated with an antibiotic such as gentamicin and applied to the critical heart/artificial cusp interface is especially suited for use as a sustained drug release system and has the additional advantage of eroding as the the drug supply is depleted, thereby eliminating the problems associated with foreign matter being present.

We have found that bioerodible polymers are useful as leave behind products in the field of abdominal surgery, particularly in dealing with surgery of the small and large intestines.

Prophylactic use of anti-infective agents such as metronidazol, has lowered the incidence of postoperative infections especially in surgery of the colon and rectum. Polymer foils, impregnated with such antibiotics, provide a means for delivering the germicidal agent locally.

A second use for these polymers in the abdominal surgery area, is in preventing postoperative adhesions, which are a serious complication in intestinal surgery. The problem rests in allowing the peritoneum to heal without also forming adhesions with the neighboring organs. Use of polymer foils, with or without a germicide, applied to the wound in the peritoneum will inhibit these adhesions.

We have also found that bioerodible polymers are useful in ocular surgery.

Following glaucoma surgery, 5-fluorouracil is given to inhibit fibroblast infiltration. Present delivery methods are by subconjunctival injections twice daily for seven days following surgery. Use of the bioerodible polymers (hard polymer) disclosed herein, formed as a device implanted at the trabeculectomy site at the time of surgery can provide controlled release of 5-fluorouracil. The implantable device can take the form of a solid rod or disc for example, and would be capable of drug delivery over a period of 7 days, where a total of about 4 mg of drug is required. The obvious benefit of this invention rests not only in the continuous drug delivery capability but also in that the device does not require removal after use, as it is bioerodible.

A second use for bioerodible polymers in the field of ocular surgery is in the area of cataract surgery. The hard polymer of this invention is especially suited for use as a controlled release bioerodible system for the delivery of epidermal growth factor (EGF) to facilitate re-epitheliazation of corneal tissue after cataract surgery. The system, in the hard polymer elliptical form, would be placed under the lower eyelid after surgery to deliver EGF for a period of 3–7 days, or longer. Alternately, the product could be formulated into a suspendable particulate dosage form comprised of particles of the bioerodible polymer (A) or polymer (B) and EGF, which could be injected subconjunctivally after the surgical procedure. This alternate method would also provide EGF drug delivery for a period of 3-7 days or longer.

Lastly, we have found that bioerodible polymers have particular use in stopping bleeding in the liver and the spleen.

Capillary and venous oozing from wounds in the liver and spleen are often extremely difficult to stop surgically. Polymer foil can be used alone in this regards, due to its hemostatic property, or alternately, the foil may be impregnated with a chemotherapeutic agent such as trombokinase.

In summary, bioerodible polymers of the structure:

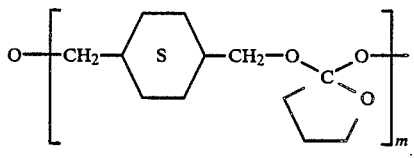

where m equal a number such that the molecular weight of the polymer is within the range of 10,000 to 60,000, used alone as a hard polymer, or formed into a polymer foil, polymer beads or other configuration, or used in combination with a bioerodible polymer of the structure:

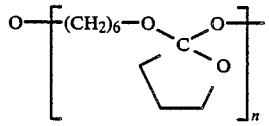

where n equals a number such that the molecular weight of the polymer is within the range of 10,000 to 60,000, as a pliable polymer (bone wax), are especially suited for various uses in the areas of orthopedic, thoracic, abdominal and ocular surgery, along with being useful in surgery of the liver and spleen.

This invention has been described in detail with particular reference to certain preferred embodiments thereof, but it will be understood that variations and modifications can be effected within the spirit and scope of the invention.

What is claimed is:

1. A method of providing hemostasis at the site of a surgical procedure comprising placing a bioerodible material in hemostatic relationship to a bleeding body substrate, maintaining said hemostatic relationship up to and after the completion of said surgical procedure, said bioerodible material being free of any chemotherapeutic agent and being selected from the group consisting of polymer (A), polymer (B), physical mixtures of polymers (A) and (B), block copolymers of (A) and (B) and random copolymers of (A) and (B), wherein said polymer (A) has the following structure:

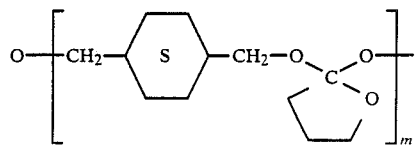

where m equals a number such that the molecular weight of polymer (A) is within the range of 10,000 to 60,000; and wherein said polymer (B) has the following structure:

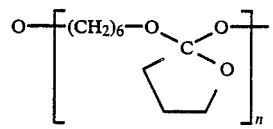

where n equals a number such that the molecular weight of polymer (B) is within the range of 10,000 to 60,000.

2. The method of claim 1, wherein said bleeding body substrate is a severed bone, said material is placed in contact with the severed bone surface, and said bioerodible material is selected from the group consisting of physical mixtures of polymers (A) and (B), block copolymers (A) and (B) and random copolymers of (A) and (B).

3. The method of claim 1, wherein said surgical procedure includes longitudinally severing a sternum, thereafter rejoining said severed sternum and placing said material in hemostatic contact with the severed sternum, said bioerodible material being selected from the group consisting of physical mixtures of polymers (A) and (B), block copolymers of (A) and (B) and random copolymers of (A) and (B).

4. The method of claim 1, wherein said surgical procedure includes severing at least a portion of a parenchymatous organ and placing said bioerodible material in contact with the severed portion of said parenchymatous organ, said bioerodible material being polymer (A).

5. The method of claim 1, wherein said bioerodible material is a foil.

6. In an orthopedic surgical procedure to lengthen a leg bone, including transversely cutting a segment of the bone, gradually distracting the cut bone segment from the bone and anchoring the cut bone segment and the bone with transcutaneous pins, the improvement which comprises:

providing a sleeve for each of the transcutaneous pins, the sleeves being comprised of a porous bioerodible material which is free of any chemotherapeutic agent and having pores of a size which permit ingrowth of fibrous tissue, said bioerodible material being a polymer having the following structure:

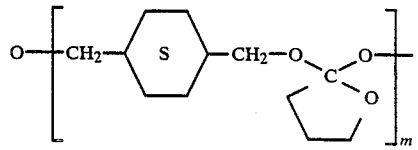

where m equals a number such that the molecular weight of said polymer is within the range of 10,000 to 60,000.

7. In method of preventing adhesion between the peritoneum and a neighboring internal organ after an abdominal surgical procedure in which the peritoneum is severed, the improvement comprising:

placing a bioerodible material which is free of any chemotherapeutic agent adjacent the severed peritoneum, said bioerodible material being selected from the group consisting of polymer (A), polymer (B), physical mixtures of polymers (A) and (B), block copolymers of (A) and (B) and random copolymers of (A) and (B), wherein said polymer (A) has the following structure:

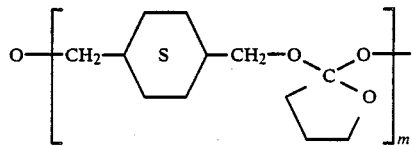

where m equals a number such that the molecular weight of polymer (A) is within the range of 10,000 to 60,000; and wherein said polymer (B) has the following structure:

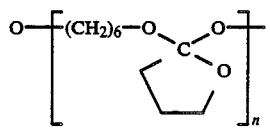

where n equals a number such that the molecular weight of polymer (B) is within the range of 10,000 to 60,000.

8. The method of claim 7, wherein said material is foil.

9. The method of claim 7, wherein said internal organ comprises an intestine.

* * * * *